… (United States Patent)

Capuzzi et al.

Patent Number: 5,905,072
Date of Patent: May 18, 1999

[54] ADJUVANTS FOR SYSTEMIC FUNGICIDES, FUNGICIDAL COMPOSITIONS WHICH CONTAIN THEM AND THEIR USE

[75] Inventors: Luigi Capuzzi, Novara; Mario Ferri, Milan; Ernesto Signorini, Malnate; Nicola Stramacchia, Milan, all of Italy; Claude Delestre, Montreuil-Bellay, France; Luigi Mirenna, Milan, Italy

[73] Assignee: Isagro S.p.A., Milan, Italy

[21] Appl. No.: 08/599,592

[22] Filed: Feb. 9, 1996

[30] Foreign Application Priority Data

Feb. 23, 1995 [IT] Italy ................. MI95A0336

[51] Int. Cl.$^6$ .......... A01N 25/00; A01N 55/10; A01N 43/50; A01N 43/40
[52] U.S. Cl. .......... 514/63; 514/231.2; 514/239.5; 514/315; 514/317; 514/359; 514/374; 514/376; 514/383; 514/384; 514/385; 514/386; 514/396; 514/399; 514/400; 514/534; 514/535; 514/538; 514/615; 514/772; 514/772.1; 514/772.3; 514/784; 514/785; 514/937; 514/941; 514/942; 514/943
[58] Field of Search .............. 514/772, 772.1, 514/772.3, 784, 785, 63, 231.2, 239.5, 315, 317, 359, 374, 376, 383–386, 396, 399, 400, 534, 535, 538, 615, 937, 941, 942, 943

[56] References Cited

U.S. PATENT DOCUMENTS 5,565,146  10/1996  Jakubicki et al. .............. 510/235

FOREIGN PATENT DOCUMENTS

| 0 379 851 | 8/1990 | European Pat. Off. . |
| 0 394 847 | 10/1990 | European Pat. Off. . |
| 0 432 062 | 6/1991 | European Pat. Off. . |
| 59 168181 | 9/1984 | Japan . |
| WO 92/06596 | 4/1992 | WIPO . |
| WO 94/23578 | 10/1994 | WIPO . |
| WO 94/24858 | 11/1994 | WIPO . |

OTHER PUBLICATIONS

Pesticide Science, vol. 37, No. 2, pp. 141–146, 1993, Richard J. Hamilton, "Structure and General Properties of Mineral and Vegetable Oils Used as Spray Adjuvants".

*Primary Examiner*—John Pak
*Attorney, Agent, or Firm*—Oblon, Spivak, McClelland, Maier & Neustadt, P.C.

[57] ABSTRACT

Adjuvants for systemic fungicides in the form of a stable microemulsion comprise water, a mixture of methyl esters of fatty acids obtained by the transesterification of vegetable oils, an anionic surface-active agent, at least one non-ionic surface-active agent with an HLB of between 13–18 and a cloud point of >65° and at least one non-ionic surface-active agent with an HLB of between 10 and 12. These adjuvants, which can additionally contain conventional components and/or formulation additives, improve the activity of systemic fungicides belonging to different chemical groups.

15 Claims, No Drawings

ADJUVANTS FOR SYSTEMIC FUNGICIDES, FUNGICIDAL COMPOSITIONS WHICH CONTAIN THEM AND THEIR USE

The present invention relates to adjuvants for systemic fungicides, fungicidal compositions which contain them and their use in agriculture.

It is common practice in agriculture to use many systemic fungicides, characterized by a high specificity, together with products, known as adjuvants, for improving and/or modifying their physico-chemical characteristics.

These adjuvants comprise vegetable or mineral oils, surface-active agents, emulsifying agents, dispersers, anti-foaming agents, antidrift agents and others. They give the fungicide positive effects such as greater coverage and endurance on the leaves, better penetration of the fungicide into the leaves and movement through the plant as well as enforcing its fungicidal activity.

In particular adjuvants consisting of 75–95% of mineral oils and 25–5% of surface-active agents are becoming more and more widely used. These adjuvants provide a better dispersion of the fungicide on the plants making the fungicide more effective.

The adjuvants of the known art however have the disadvantage of being phytotoxic and are not biodegradable.

In addition, the necessity has been felt in the art of having adjuvants with a wide range of action, i.e. capable of improving the activity of systemic fungicides belonging to different chemical groups.

It has now been found that these requirements can be fulfilled by the adjuvants of the present invention which contain water, a mixture of methyl esters of fatty acids deriving from the transesterification of vegetable oils, an anionic surface-active agent, at least one non ionic surface-active agent with an HLB of between 13 and 18 and a cloud point of >65°C., one or more non ionic surface-active agents with an HLB of between 10 and 12 or a mixture of these with an average HLB of between 10 and 12.

In particular it has been found that the combination of the mixture of methyl esters of fatty acids deriving from the transesterification of vegetable oils with suitable surface-active agents has a synergic effect on the activity of systemic fungicides belonging to different chemical groups.

In accordance with this, the present invention relates to adjuvants for systemic fungicides in the form of a stable microemulsion, which comprise:

(a) water in a quantity of between 10 and 30% by weight;
(b) a mixture of methyl esters of fatty acids deriving from the transesterification of vegetable oils in a quantity of between 20 and 50% by weight;
(c) an anionic surface-active agent selected from the group consisting of alkyl sulfosuccinates, alkyl benzene sulfonates or their metallic salts in a quantity of between 0.5 and 20% by weight;
(d) at least one non-ionic surface-active agent with an HLB of between 13 and 18 and with a cloud point of >65° C. selected from alkyl polyglucosides, alkyl polyether polyglucosides and polystyrylphenol polyalkoxylates; and
(e) at least one non-ionic surface-active agent with an HLB of between 10 and 12 selected from sorbitan esters of fatty acids and products deriving from the condensation of an alkylenic oxide, preferably ethylene or propylene, with organic compounds having an active hydrogen such as $C_{10}$–$C_{20}$ fatty alcohols, amides, esters and $C_6$–$C_{12}$ alkyl phenols, or mixtures of these having an average HLB of between 10 and 12; and where the weight ratio between the mixture of methyl esters (b) and the surface-active agents (c), (d) and (e) is between 0.8:1 and 1.2:1.

In the present invention HLB means the hydrophilic-lipophilic balance of a surface-active agent: the greater the HLB value the greater the solubility of the surface-active agent in water.

Mixtures of methyl esters of fatty acids which are suitable for the purposes of the present invention are those deriving from the transesterification of vegetable oils such as soyabean, colza, sunflower and their mixtures. Preferred is a mixture of methyl esters of fatty acids obtained from the transesterification of colza oil having:

| | |
|---|---|
| Content of monoglycerides | Max. 1.0% by weight |
| Content of diglycerides | Max. 0.3% by weight |
| Content of triglycerides | Max. 0.1% by weight |
| Free glycerine | Max. 0.1% by weight |
| Methanol | Max. 0.3% by weight |
| Iodine number | Max. 115 |
| Density | 0.86–0.90 g/cc |
| Viscosity at 40° C. | 3.5–5.0 cS |
| Flash point | Min. 100° C. |

A mixture with these characteristics is available on the market under the trade-name of Diesel$^R$ Bi(TM) (Novamont S.p.A.).

Anionic surface-active agents which can be used for the purposes of the present invention are selected from alkylbenzenesulfonates or, preferably, alkylsulfosuccinates and their metal salts.

These surface-active agents can be prepared with the conventional techniques. In particular, alkylsulfosuccinates can be conveniently prepared by the esterification of maleic acid or maleic anhydride with one or two moles, preferably two, of an aliphatic alcohol with a number of carbon atoms of between 2 and 20. Particularly preferred is 2-ethylenhexanol alcohol. The reaction product between maleic anhydride and this alcohol, known under the name of dioctylsulfosuccinate, is the anionic surface-active agent which is particularly preferred for the purposes of the present invention.

The surface-active agents are generally used in a quantity of between 0.5 and 20%, preferably 1–10%, by weight with respect to the total weight of the composition.

Examples of non-ionic surface-active agents with an HLB of between 13 and 18 are alkyl polyglucosides (APG) ($C_{10}$–$C_{16}$ ethers of pyranosides or oligomers), alkyl polyethers polyglucosides (AEG) ($C_{10}$–$C_{12}$ polyethoxylated ethers of pyranosides or oligomers) or, preferably, mixtures of these provided that the resulting mixture has the above HLB values or polyethoxylated polystyrylphenols, such as for example polyethoxylated tristyrylphenol with a number of ethylene oxide moles of between 16 and 40, preferably 16–25. These surface-active agents are generally used in quantities of between 5 and 20% by weight with respect to the composition.

Examples of non-ionic surface-active agents which are suitable for the purposes of the present invention are selected from:

(i) sorbitan esters of fatty acids such as, for example, sorbitan monolaurate, sorbitan monopalmitate, sorbitan mono-oleate, sorbitan monostereate, sorbitan trioleate and sorbitan tristereate; sorbitan monooleate is preferred, or
(ii) products deriving from the condensation of an ethylene oxide with:
a fatty alcohol, such as for example, decyl, tridecyl, lauryl or stearyl alcohol with a number of ethylene oxide molecules of between 5 and 10.

polyethoxylated sorbitan esters such as for example sorbitan monolaurate (4–20 moles of ethylene oxide (EtO), sorbitan monopalmitate (20 EtO), sorbitan mono-oleate (20 EtO), sorbitan monostereate (4–20 EtO), sorbitan trioleate (20 EtO) and sorbitan tristereate (20 EtO). Sorbitan mono-oleate 20 EtO also known as Tween-80, is preferred.

$C_6$–$C_{12}$ alkylphenols with a number of ethylene oxide molecules of between 2 and 20, such as for example nonylphenol; and amides.

These surface-active agents are used in quantities of between 5 and 25%, preferably between 10 and 15% by weight with respect to the composition. Mixtures of these non-ionic surface-active agents are preferred for the purposes of the present invention, provided that these mixtures have an HLB of between 10 and 12.

The adjuvants of the present invention can additionally contain special additives for particular purposes such as adhesive agents such as arabic rubber, polyvinyl alcohol, polyvinylpyrrolidone, antifreeze agents such as propylenglycol, antifoaming or antidrift agents used in quantities of between 0 and 15% by weight.

The adjuvants of the present invention increase the activity of systemic fungicides belonging to different groups such as:

triazolic: tetraconazole, triadimefon, triadimenol, propiconazole, diclobutrazol, biternatol, penconazole, flutriafol, hexaconazole, myclobutanyl, flusilazole cyproconazole, diniconazole, difenocaonazole, epoxiconazole;

imidazolic: prochloraz, imazalil;

morpholinic: fenpropimorph; tridemorph dicarboxyimidic: iprodione, chlozolinate, vinclozolin piperidinic: fenpropidin and acylalanicinic: metalaxyl, benalaxyl.

The adjuvants of the present invention are particularly effective with systemic fungicides belonging to the group of triazolic compounds (tetraconazol), dicarboxyimidic compounds (chlozolinate) and acylalaninic compounds (benalaxyl).

These adjuvants enable the quantity of systemic fungicide to be substantially reduced to obtain the desired effect or, with the same dosage, to obtain a higher level of activity. In addition, these adjuvants allow better results to be obtained compared to the adjuvants of the known art.

The fungicidal compositions obtained by combining the adjuvants of the present invention with one or more systemic fungicides have a particularly high fungicidal activity against phytopathogen fungi which attack cultivations of cereals, cucurbitaceae, vines and fruit trees.

Examples of plant diseases which can be fought with the fungicidal compositions are the following:

*Erysiphe graminis* of cereals;

*Sphaeroteca fuliginea* of cucurbitaceae (for example cucumber);

Puccinia of cereals;

Septoria of cereals;

Helminthosporium of cereals;

Rhynchosporium of cereals;

*Podosphaera leucotricha* of apple trees;

*Plasmopora viticola* of vines;

*Phytophtora infestans* of tomatoes;

*Uncinula necator* of vines;

*Venturia inaeqoualis* of apple trees;

*Piricularia oryzae* of rice;

*Botrytis cinerea;*

Fusarium of cereals.

These fungicidal compositions can be applied to any part of the plants, for example leaves, stems, branches and roots, or on the seeds themselves before being planted, or on the soil in which the plant grows.

When the plants are treated, a suitable quantity of fungicide or, alternatively, commercial formulations containing said fungicide can be added to the adjuvant. These commercial formulations are generally emulsifiable liquids, wettable powders, concentrated suspensions, water emulsions or microemulsions. The adjuvants of the present invention are conveniently added in quantities of between 0.01 and 0.5%, preferably between 0.05 and 0.3% by weight.

The preferred source of the active systemic fungicidal principle consists of a commercial formulation which contains it and which is used in relation to the application with the minimum dosages recommended by the producer.

According to a particular form of embodiment of the present invention, concentrated fungicidal compositions ready for dilution containing one or more systemic fungicides and the adjuvant of the present invention, can also be prepared. The availability of these formulations allows a correct dosage of the active principle and adjuvant, thus reducing the risks deriving from the handling of unexperienced operators.

The fungicidal composition can also contain a cover fungicide such as Mancozeb, copper oxychloride, thiram fentin hydroxide. The preferred source of this second active principle can be a commercial formulation containing it. Alternatively, commercial formulations containing a systemic fungicide and a cover fungicide can be used.

If desired, it is possible to also add other compatible active substances such as phytodrugs, phytoregulators, weed-killers, insecticides and fertilizers, to the fungicidal compositions of the present invention.

A positive characteristic of the adjuvants of the present invention consists in the possibility of obtaining good performances from the application of the active principles even when it rains immediately after treatment.

In the following experimental examples the adjuvant Comp.A and the fungicidal composition Form.B ready for use, the characteristics of which are listed below, were used.

Comp. A

| | |
|---|---|
| Diesel Bi | 43% |
| Nonylphenol | 02 EtO 3% (HLB = 4.7) |
| Nonylphenol | 04 EtO 1% (HLB = 8.9) |
| Nonylphenol | 10 EtO 10% (HLB = 13.3) |
| Isotridecyl alcohol | 10 EtO 8% (HLB = 12.1) |
| Stearyl alcohol | 9 EtO 10% (HLB = 10.6) |
| | average 11.2 |
| Dioctyl sulfosuccinate | 1% |
| Mixture of alkyl polyglycoside and alkyl polyether polyglycoside | 10% |
| Water | 14% |

The microemulsion has the following characteristics:

Appearance: transparent microemulsion

Colour: bright yellow-gold

Density (20° C.): 0.959–0.961

Kinematic viscosity: about 120 cS

Heat stability: 1 month at 54° C. unaltered

Cold stability: 1 week at −7° C. unaltered

Form. B

| | |
|---|---|
| Tetraconazol | 12.5% |
| Diesel Bi | 25.0% |
| Tristyryl phenol 17 EtO | 12.5% |
| Sorbitan mono-oleate 20 Eto | 5.0% |
| Sorbitan mono-oleate | 2.5% |
| Dicotyl sulfosuccinate | 7.0% |
| Propylenglycol | 15.0% |
| Water | 20.5% |

The microemulsion has the following characteristics:

Appearance: transparent microemulsion

Colour: bright yellow-gold

Density (20° C.): 1.043 pH=6.5

Kinematic viscosity: 110 cS

Heat stability:
   1 month at 54° C. unaltered
   3 months at 45° C. unaltered
   6 months at 40° C. unaltered Cold stability:
   1 week at −7° C. slight reversible opalescence Dilution stability (0.5–2% in water): stable opalescent solution The following examples provide a better illustration of the present invention without restricting its scope in any way.

EXAMPLE 1

Barley seeds Plaisant are left to germinate in a vase having a diameter of 11 cm containing a mixture 1:1 of earth:sand and grown in a cell climatized at 21° C., 70% humidity. After 7 days an artificial infection is carried out by spraying onto the leaves an aqueous suspension of *Puccinia hordei* (500 mg of spores/l) containing Tween 20 (0.1%). The plants are transferred to a saturated environment at a temperature of 20° C. for 24 hours and subsequently kept in a green-house at 20–25° C. with a humidity of 60–80% for 2 days.

The plants are then treated, using a horizontal rod equipped with a sprayer at a distance of 50 cm from the leaves, with a volume of water equal to 1000 l/ha having the following composition:

| | |
|---|---|
| Water | 1000 l/ha |
| Comp. A | 2 l/ha |
| tetraconazol | 7.5–30 g/ha |

The commercial formulation EMINENT$^R$ containing 125 g/l of tetraconazol is used as the source of active principle. After 14 days, during which the plants are maintained in a conditioned environment, the gravity of the attack is estimated, by observing the evasion of the pathogen, with evaluation indexes from 0 (no protection) to 100 (full protection). The results are shown in table 1 below:

TABLE 1

| Product | A. P. dosage ppm | Comp. A ppm | Infection % | Protection % |
|---|---|---|---|---|
| Control | 0 | 0 | 96 | 0 |
| EMINENT | 30 | 0 | 27 | 72 |
| " | 15 | 0 | 65 | 37 |

TABLE 1-continued

| Product | A. P. dosage ppm | Comp. A ppm | Infection % | Protection % |
|---|---|---|---|---|
| " | 7.5 | 0 | 75 | 22 |
| " | 30 | 2000 | 1 | 99 |
| " | 15 | 2000 | 3 | 97 |
| " | 7.5 | 2000 | 19 | 80 |

A. P. means active part.

EXAMPLE 2

The same procedure is carried out as in example 1, using the commercial formulation ARPEGE$^R$ containing 100 g/l of tetraconazol as source of the active principle in the treatment phase.

Half of the plants are treated with the following composition:

| | |
|---|---|
| Water | 1000 l/ha |
| Comp. A | 2 l/ha |
| tetraconazol | 7.5–30 g/ha | whereas the other half is treated with the composition:

| | |
|---|---|
| Water | 1000 l/ha |
| Comp. A | 2 l/ha |
| tetraconazol | 50.100 g/ha | and, after 30 minutes from the treatment, it is subjected to washing away for 4 hours simulating a rain-fall equal to 60 mm.

The results are shown in table 2 below:

TABLE 2

| Product | A. P. dosage ppm | Comp. A ppm | Washing | Protection % |
|---|---|---|---|---|
| Control | 0 | 0 | no | 0 |
| ARPEGE | 30 | 0 | no | 75 |
| " | 15 | 0 | no | 65 |
| " | 7.5 | 0 | no | 33 |
| " | 100 | 0 | yes | 67 |
| " | 50 | 0 | yes | 23 |
| " | 30 | 2000 | no | 92 |
| " | 15 | " | no | 82 |
| " | 7.5 | " | no | 71 |
| " | 100 | " | yes | 95 |
| " | 50 | " | yes | 88 |

EXAMPLE 3

Wheat seeds Gemini are left to germinate in a vase containing a mixture of earth:sand (1:1) and cultivated in a cell climatized at 21° C., 70% humidity. After 7 days the leaves are sprayed with an aqueous suspension of *Puccinia graminis* (500 mg of spores/l) containing Tween 20 (0.1%). The plants are transferred to a saturated environment at a temperature of 20° C. for 24 hours and subsequently kept in a greenhouse at 20–25° C. with a humidity of 60–80%.

After 2 days the leaves are sprayed with a volume of water equal to 1000 l/ha with the following composition:

| | |
|---|---|
| Water | 1000 l/ha |
| Comp. A | 0.5–2 l/ha |
| tetraconazol | 3.7–15 g/ha |
| fenpropimorph | 11.1–45 g/ha |

After 14 days, during which the plants are kept in a conditioned environment, the gravity of the attack is estimated, by observing the evasion of the pathogen, with evaluation indexes from 0 to 100.
The results are shown in table 3 below.

TABLE 3

| TCN/FPM ppm | Comp: A ppm | % Protection |
|---|---|---|
| Control | 0 | 0 |
| 15/45 | 0 | 87 |
| 7.5/22.5 | " | 73 |
| 3.7/11.1 | " | 50 |
| 15/45 | 500 | 99 |
| 7.5/22.5 | " | 87 |
| 3.7/11.1 | " | 63 |
| 15/45 | 1000 | 96 |
| 7.5/22.5 | " | 90 |
| 3.7/11.1 | " | 73 |
| 15/45 | 2000 | 100 |
| 7.5/22.5 | " | 95 |
| 3.7/11.1 | " | 83 |

EXAMPLE 4

Tomatoes Marmande are cultivated in vases with a diameter of 11 cm containing a mixture 1:1 of sterilized earth: compost for horticulture for about a month. When the plants reach the stage of 5 full leaves, they are infected by spraying on the lower part of the leaves an aqueous suspension of sporangia of *Phytopheora infestans* taken from infected leaves ($2\times10^5$/ml). The plants are then transferred to a humidity saturated environment, at a temperature of 20° C. After 1 day, half of the plants are treated by spraying with a commercial formulation (Galben$^R$ M) comprising 8% of Benalaxyl and 65% of Mancozeb, and the other half with the same formulation to which adjuvant A (2000 ppm) has been added. After 4 hours the leave are detached and placed, with the lower part facing upwards, onto plates containing two filter-paper disks dampened with sterile water. After 3 days at 20° C., the evasion percentage of the pathogen is evaluated. The results are shown in table 4 below.

TABLE 4

| Product | A. P. dosage ppm | Comp. A ppm | Infection % | Protection % |
|---|---|---|---|---|
| Control | 0 | 0 | 100 | 0 |
| Galben M | 500/4000 | 0 | 45 | 55 |
| " | 125/1000 | 0 | 40 | 60 |
| " | 30/240 | 0 | 54 | 46 |
| " | 500/4000 | 2000 | 8 | 92 |
| " | 125/1000 | 2000 | 2 | 88 |
| " | 30/240 | 2000 | 42 | 58 |

EXAMPLE 5

Deep-rooted cuttings of six-week-old dolcetto vines are infected by spraying on the lower part of the leaves an aqueous suspension of zoosporangia of *Plasmopara viticola* taken from infected leaves ($2\times10^5$/ml). The plants are then transferred to a humidity saturated environment at 20° C. After 1 day the plants are treated with Galben M with or without the addition of the adjuvant Comp.A and, subsequently, transferred to a greenhouse at 20° C., 60–80% humidity. After six days the humidity is brought to 100% and after 24 hours the evasion percentage of the pathogen is evaluated. The results are shown in table 5.

TABLE 5

| Product | A. P. dosage ppm | Comp. A ppm | Infection % | Protection % |
|---|---|---|---|---|
| Control | 0 | 0 | 100 | 0 |
| Galben M | 7.5/60 | 0 | 1 | 99 |
| " | 1.8/15 | 0 | 92 | 8 |
| " | 7.5/60 | 2000 | 0 | 100 |
| " | 1.8/15 | 2000 | 0 | 100 |

EXAMPLE 6

The same procedure is carried out as in example 1, using a formulation containing tetraconazol and copper oxychloride with varying dosages, in the treatment phase.

For comparative purposes the test is repeated with equal quantities of adjuvant based on white mineral oil. The results are shown in table 6 below.

TABLE 6

| Product | A. P. dosage ppm | Vaseline ppm | Comp. A ppm | Protection % |
|---|---|---|---|---|
| Control | 0 | 0 | 0 | 0 |
| Tet/Cu | 30.0/540 | 0 | 0 | 18 |
| " | 15.0/270 | 0 | 0 | 11 |
| " | 7.5/135 | 0 | 0 | 3 |
| Tet/Cu | 30.0/540 | 0 | 2000 | 73 |
| " | 15.0/270 | 0 | 2000 | 62 |
| " | 7.5/135 | 0 | 2000 | 45 |
| Tet/Cu | 30.0/540 | 2000 | 0 | 60 |
| " | 15.0/270 | 2000 | 0 | 45 |
| " | 7.5/135 | 2000 | 0 | 25 |

EXAMPLE 7

The same procedure is adopted as in example 6, carrying out, 30 minutes after the treatment, a washing away for 4 hours with rain equal to a fall of 60 mm.

The results are shown in Table 7 below.

TABLE 7

| Product | A. P. dosage ppm | Vaseline ppm | Comp. A ppm | Protection % |
|---|---|---|---|---|
| Control | 0 | 0 | 0 | 0 |
| Tet/Cu | 100/1800 | 0 | 0 | 27 |
| " | 50/990 | 0 | 0 | 9 |
| Tet/Cu | 100/1800 | 0 | 2000 | 76 |
| " | 50/900 | 0 | 2000 | 63 |
| Tet/Cu | 100/1800 | 2000 | 0 | 60 |
| " | 50/900 | 2000 | 0 | 45 |

EXAMPLE 8 (comparative)

The same procedure is carried out as in example 1 using, for comparative purposes, equal quantities of a commercial adjuvant based on mineral oil (A), a commercial adjuvant based on vegetable oil (B), Diesel Bi and the mixture of surface-active agents using for the preparation of the additive Comp.A. The results, expressed as ED 90 (dosage at which 90% protection is verified), are shown in table 8 below.

TABLE 8

| Product | Adjuvant | ED 90 ppm |
|---|---|---|
| Eminent | 0 | 75 |
| Eminent | Comp. A 2000 ppm | 15 |
| " | Comp. A 1000 ppm | 25 |
| Eminent | Diesel Bi 2000 ppm | 35 |
| " | Diesel Bi 1000 ppm | 50 |
| Eminent | Surf.-act. agent 2000 ppm | 40 |
| " | Surf.-act. agent 1000 ppm | 65 |
| Eminent | A 2000 ppm | 30 |
| " | B 2000 ppm | 45 |

EXAMPLE 9

Tests are carried out on site in a vineyard Muller turgau using the following compositions:

| | | |
|---|---|---|
| (a) Serinal$^R$ PB 50 (chiozolinate) | 200 g/hl | |
| (b) Serinal$^R$ PB 50 | 150 g/hl | |
| (c) Serinal$^R$ PB 50 | 150 g/hl + Comp. A 100 g/hl | |
| (d) Serinal$^R$ PB 50 | 150 g/hl + Comp. A 200 g/hl | |
| (e) Serinal$^R$ PB 50 | 100 g/hl + Comp. A 200 g/hl | |

5 tests are carried out for each composition on groups of 7 plants each.

The treatment is carried out, using an EKU shoulder-pump, by spraying 20 liters of the above compositions during the stage comprising the end of blossoming, preclosing of the grape-cluster and ripening. 45 days after the last treatment the degree of infection by *Botrytis cinerea* is evaluated. In practice, the plants are assigned, in relation to the intensity of the disease, to one of the eight groups into which the degree of infection is subdivided and wherein the lowest (N0) contains the plants with clusters having no signs of grey mould, and the highest (N7) those with clusters having from 91 to 100% of the surface covered with grey mould. The index of the disease (I %) is calculated by means of the following formula:

$$I\% = \frac{N^1 x1 + N^2 x2 + N^3 x3 + \ldots N^7 \times 100}{(N0 + N^1 + N^2 + \ldots N^7) \times 7}$$

wherein $N^1$–$N^7$ represent the number of infected clusters assigned to each group.

Table 9 shows the infection index and statistical analysis. comparison is made with non-treated plants (f).

TABLE 9

| Compound | Infection index | Statistical group |
|---|---|---|
| (a) | 25.7% | bc |
| (b) | 31.2% | bc |
| (c) | 20.8% | c |
| (d) | 21.7% | c |
| (e) | 37.8% | b |
| (f) | 64.0% | a |

The use of the adjuvant Comp.A allows a saving of the active principle (Serinal 50 PB) of at least 25%.

EXAMPLE 10

The same procedure is carried out as in example 1, using the fungicidal composition Form.A in the treatment phase and as a comparison the commercial formulation Eminent.

TABLE 10

| Product | A. P. dosage ppm | % Infection | % Protection |
|---|---|---|---|
| Control | 0 | 91.6 | 0 |
| Eminent | 240 | 21.6 | 76 |
| " | 120 | 31 | 66 |
| " | 60 | 49.9 | 45 |
| " | 30 | 57.2 | 37 |
| " | 15 | 71.7 | 22 |
| Form. A | 240 | 15.3 | 83 |
| " | 120 | 18.0 | 80 |
| " | 60 | 22.3 | 76 |
| " | 30 | 24.0 | 73 |
| " | 15 | 40.2 | 56 |

From the above data it can be seen that the effect of the fungicidal composition of the present invention is more effective than the comparative formulation, above all at lower dosages.

EXAMPLE 11

The same procedure is adopted as in example 10, carrying out, 30 minutes after treatment, a washing away with artificial rain equal to a fall of 60 mm. The results are shown in table 11.

TABLE 11

| Product | A. P. dosage ppm | % Infection | % Protection |
|---|---|---|---|
| Control | 0 | 95.0 | 0 |
| Eminent | 100 | 50.7 | 47 |
| " | 50 | 69.6 | 27 |
| Form. B | 100 | 34.4 | 64 |
| " | 50 | 44.6 | 53 |

We claim:
1. An adjuvant in the form of a stable microemulsion comprising:
 (a) water in a quantity of between 10 and 30% by weight;
 (b) a mixture of methyl esters of fatty acids deriving from the transesterification of vegetable oils in a quantity of between 20 and 50% by weight;
 (c) an anionic surface-active agent selected from the group consisting of alkyl benzene sulfonates, alkylsulfosuccinates and their metal salts;
 (d) at least one non-ionic surface-active agent with an HLB of between 13 and 18 and with a cloud point of >65° C. selected from the group consisting of alkyl polyglucosides, alkyl polyether polyglucosides and polystyryl-phenol polyalkoxylates; and
 (e) at least one non-ionic surface-active agent with an HLB of between 10 and 12 selected from the group consisting of sorbitan esters of fatty acids and products deriving from the condensation of an alkylenic oxide with organic compounds having an active hydrogen, said organic compounds selected from the group consisting of fatty alcohols with a number of carbon atoms $C_{10}$–$C_{20}$, amides, esters and $C_6$–$C_{12}$ alkyl phenols, with a weight ratio between the mixture of methyl esters (b) and the surface-active agents (c), (d) and (e) of between 0.85:1 and 1.2:1.
2. The adjuvant according to claim 1, characterized in that the mixture of methyl esters of fatty acids has:.

| | |
|---|---|
| Content of monoglycerides | Max. 1.0% by weight |
| Content of diglycerides | Max. 0.3% by weight |
| Content of triglycerides | Max. 0.1% by weight |
| Free glycerine | Max. 0.1% by weight |
| Methanol | Max. 0.3% by weight |
| Iodine number | Max. 115 |
| Density | 0.86–0.90 g/cc |
| Viscosity at 40° C. | 3.5–5.0 cS |
| Flash point | Min. 100° C. |

3. The adjuvant according to claim 1, characterized in that the anionic surface-active agent (c) is dioctylsulfosuccinate.

4. The adjuvant according to claim 1, characterized in that the non-ionic surface-active agent (d) is selected from the group consisting of alkyl ($C_{10}$–$C_{16}$) polyglucosides, alkyl polyether polyglucosides and polystyrylphenol polyethoxylates with a number of ethylene oxide moles of between 16 and 40.

5. The adjuvant according to claim 4, characterized in that the polyethoxylated polystyrylphenol is polyethoxylated tristyrylphenol with a number of ethylene oxide moles of between 16 and 25.

6. The adjuvant according to claim 1, characterized in that the non-ionic surface-active agent (e) is at least one selected from the group consisting of sorbitan monolaurate, sorbitan monopalmitate, sorbitan mono-oleate, sorbitan monostereate, sorbitan trioleate, sorbitan tristearate, polyethoxylated decyl, tridecyl, lauryl and stearyl alcohol with a number of ethylene oxide moles of between 2 and 20 and $C_6$–$C_{12}$ alkylphenols with a number of ethylene oxide moles of between 2 and 20.

7. The adjuvant according to claim 6, characterized in that the non-ionic surface-active agent(e) is selected from the group consisting of sorbitan mono-oleate, isotridecyl and stearyl alcohol with a number of ethylene oxide moles of between 5 and 20 and nonylphenol with a number of ethylene oxide moles of between 2 and 10.

8. The adjuvant according to claim 1, characterized in that it additionally contains an additive selected from the group consisting of adhesive agents, anti-freeze agents, and anti-foaming and antidrift agents, used in quantities of between 0 and 15% by weight.

9. A fungicidal composition containing an adjuvant according to claim 1 and as active principle at least one systemic fungicide selected from the group consisting of triazolic, imidazolic, morpholinic, dicarboximidic, piperidinic derivatives and phenylamides.

10. The fungicidal composition according to claim 9, characterized in that the active principle is selected from the group consisting of tetraconazole, triadimefon, triadimenol, propiconazole, diclobutrazol, bitertanol, penconazole, flutriafol, hexaconazole, myclobutanyl, flusilazole, cyproconazole, diniconazole, difenoconazole, epoxiconazole, prochloraz, imazalil, fenpropimorph, tridemorph, iprodione, chlozolinate, vinclozolin, fenpropidin, metalaxyl and benalaxyl.

11. The fungicidal composition according to claim 9, characterized in that the active principle is selected from the group consisting of tetraconazole, chlozolinate and benalaxyl.

12. The fungicidal composition according to claim 9, characterized in that it additionally contains a cover fungicide.

13. A fungicidal composition obtained by mixing a systemic fungicide selected from the group consisting of triazolic, imidazolic, morpholinic, dicarboximidic, piperidinic derivatives and phenylamides or a formulation containing it with an adjuvant according to claim 1 and diluting it with a quantity of water which is sufficient to obtain the desired quantities of fungicide and adjuvant.

14. Method for fighting fungal infections comprising applying on plants, leaves, stems, branches, roots, or on seeds before sowing or on the soil in which the plant grows, a fungicidal composition as defined in claim 9.

15. The adjuvant according to claim 8, wherein the adhesive agent is selected from the group consisting of arabic rubber, polyvinyl alcohol and polyvinylpyrrolidone, and wherein the antifreeze agent is propylene glycol.

* * * * *